(12) United States Patent
Kieslich

(10) Patent No.: US 10,251,421 B2
(45) Date of Patent: Apr. 9, 2019

(54) HEATING DEVICE FOR A SMOKE-FREE CIGARETTE

(71) Applicant: S.A.S.C. AG, Baar (CH)

(72) Inventor: Dirk Kieslich, Plettenberg (DE)

(73) Assignee: S.A.S.C. AG, Baar (CH)

( * ) Notice: Subject to any disclaimer, the term of this patent is extended or adjusted under 35 U.S.C. 154(b) by 0 days.

(21) Appl. No.: 15/525,113

(22) PCT Filed: Sep. 11, 2015

(86) PCT No.: PCT/EP2015/070831
§ 371 (c)(1),
(2) Date: Jun. 16, 2017

(87) PCT Pub. No.: WO2016/071027
PCT Pub. Date: May 12, 2016

(65) Prior Publication Data
US 2018/0092399 A1   Apr. 5, 2018

(30) Foreign Application Priority Data

Nov. 7, 2014   (DE) .......... 10 2014 116 258

(51) Int. Cl.
*A24F 13/00* (2006.01)
*A24F 17/00* (2006.01)
(Continued)

(52) U.S. Cl.
CPC .......... *A24F 47/006* (2013.01); *A24F 47/002* (2013.01); *A61M 11/047* (2014.02); *A61M 15/06* (2013.01); *F24V 30/00* (2018.05)

(58) Field of Classification Search
CPC .............................. A24F 47/006; A24F 47/00
(Continued)

(56) References Cited

U.S. PATENT DOCUMENTS

| | | | | |
|---|---|---|---|---|
| 4,149,548 A | * | 4/1979 | Bradshaw | A61M 31/00 126/263.07 |
| 5,095,921 A | * | 3/1992 | Losee | A24F 47/008 128/200.19 |

(Continued)

FOREIGN PATENT DOCUMENTS

| | | |
|---|---|---|
| DE | 626 744 C | 3/1936 |
| DE | 103 21 379 A1 | 12/2004 |

(Continued)

OTHER PUBLICATIONS

International Search Report of PCT/EP2015/070831, dated Apr. 13, 2016.

*Primary Examiner* — Abdullah A Riyami
*Assistant Examiner* — Thang H Nguyen
(74) *Attorney, Agent, or Firm* — Collard & Roe, P.C.

(57) ABSTRACT

A heating device for a smoke-free cigarette is substantially made up of a liquid container and/or a reaction element, separated from one another by a destructible seal and filled with substances, the mixing of which triggers an exothermic reaction. A pin composed of heat-conductive plastic or metal is provided on the reaction element, which pin interacts with the seal, and onto which a profile body is set. The profile body is produced from an earth alkali metal, calcium chloride, calcium chloride, magnesium sulfate, sodium hydroxide or calcium oxide.

4 Claims, 12 Drawing Sheets

Figure 1:
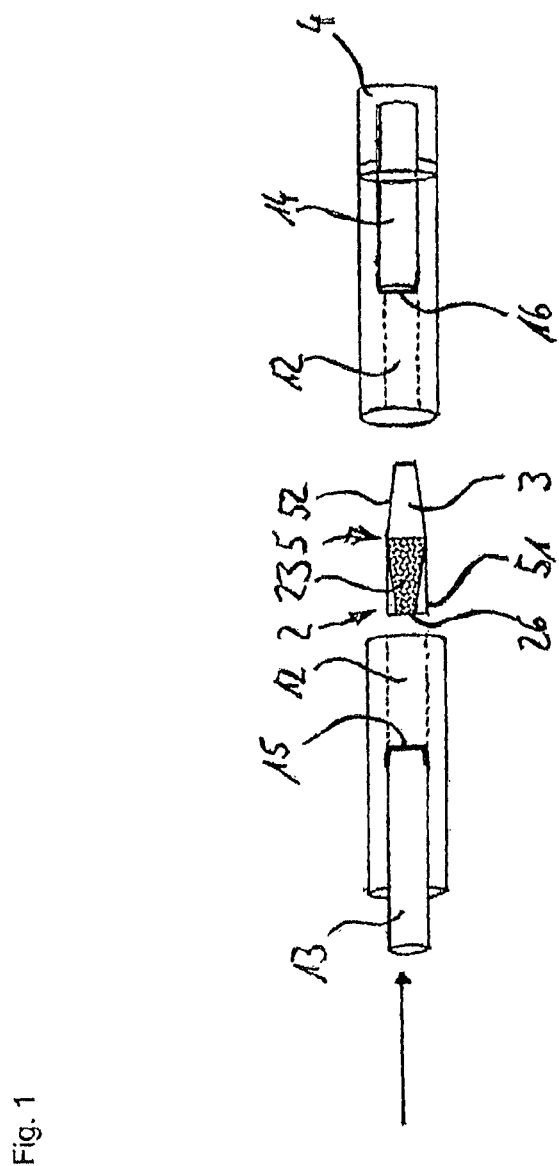

(51) Int. Cl.
*A24F 15/00* (2006.01)
*A24F 47/00* (2006.01)
*A61M 15/06* (2006.01)
*A61M 11/04* (2006.01)
*F24V 30/00* (2018.01)

(58) Field of Classification Search
USPC .................................................... 131/329
See application file for complete search history.

(56) References Cited

U.S. PATENT DOCUMENTS

| | | | | |
|---|---|---|---|---|
| 5,865,186 | A * | 2/1999 | Volsey, II | A24F 47/006 131/194 |
| 2003/0209240 | A1* | 11/2003 | Hale | A24F 47/006 128/200.24 |
| 2005/0016549 | A1* | 1/2005 | Banerjee | A24B 15/16 131/194 |
| 2006/0118128 | A1 | 6/2006 | Hoffmann et al. | |
| 2009/0151717 | A1* | 6/2009 | Bowen | A61M 11/041 128/200.23 |
| 2012/0255567 | A1* | 10/2012 | Rose | A61K 9/12 131/273 |
| 2013/0061861 | A1* | 3/2013 | Hearn | A24F 47/006 131/329 |
| 2014/0069424 | A1 | 3/2014 | Poston et al. | |
| 2015/0196060 | A1* | 7/2015 | Wensley | F22B 1/288 392/390 |
| 2015/0223520 | A1* | 8/2015 | Phillips | A61M 15/06 131/328 |
| 2016/0029694 | A1* | 2/2016 | Clements | A24F 47/004 131/329 |

FOREIGN PATENT DOCUMENTS

| | | | |
|---|---|---|---|
| DE | 10 2011 111999 A1 | 2/2013 | |
| WO | 2013/128176 A1 | 9/2013 | |
| WO | WO2013128176 * | 9/2013 | ............ A24F 47/00 |
| WO | 2014/045024 A2 | 3/2014 | |

* cited by examiner

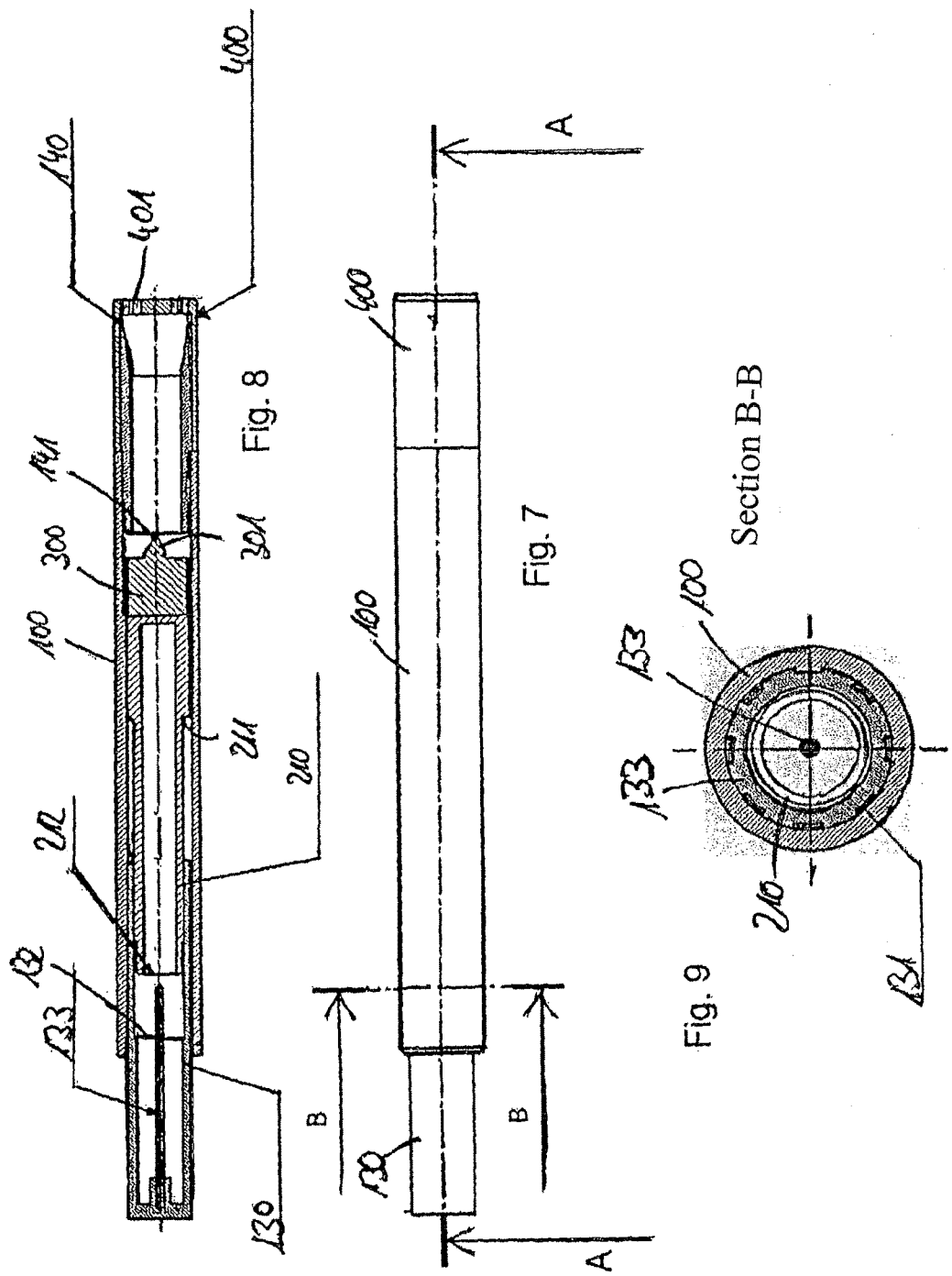

Section C-C

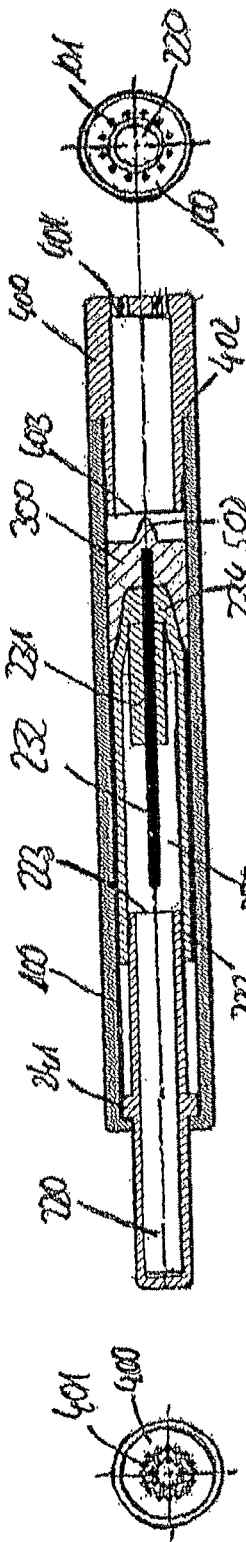
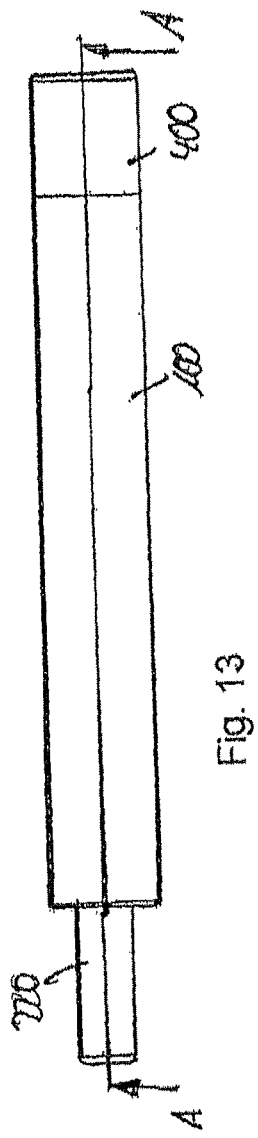
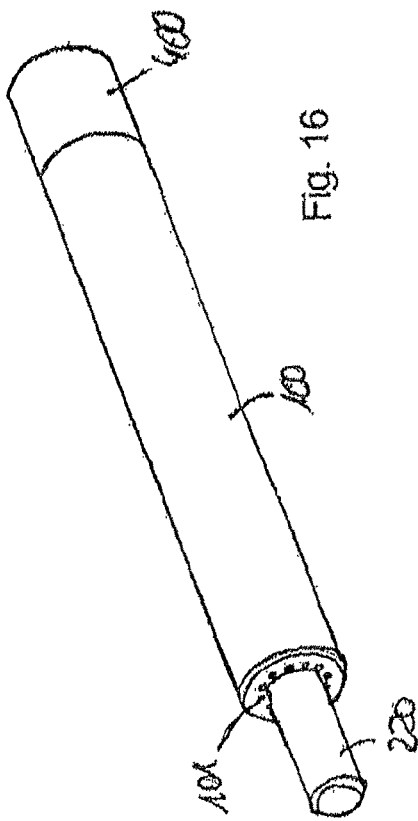

HEATING DEVICE FOR A SMOKE-FREE CIGARETTE

CROSS REFERENCE TO RELATED APPLICATIONS

This application is the National Stage of PCT/EP2015/070831 filed on Sep. 11, 2015, which claims priority under 35 U.S.C. § 119 of German Application No. 10 2014 116 258.7 filed on Nov. 7, 2014, the disclosure of which is incorporated by reference. The international application under PCT article 21(2) was not published in English.

BACKGROUND OF THE INVENTION

1. Field of the Invention

The invention relates to a heating apparatus for a smoke-free cigarette. Furthermore, the invention relates to use of a heating apparatus in a smoke-free cigarette, as well as to a smoke-free cigarette having a heating apparatus.

2. Description of the Related Art

Traditional cigarettes generally consist of tobacco wrapped in paper or in a tobacco leaf, as well as a filter element affixed on the mouthpiece. By means of igniting the end of the cigarette, the tobacco burns up and carbonizes and releases nicotine, which is entrained by the smoke to be inhaled by the smoker. During combustion of the tobacco, not only nicotine but also other substances are released or produced, which are frequently harmful to health, such as, for example, tar, compounds containing arsenic and cadmium, as well as carcinogenic compounds such as hydrazine, chrysene, formaldehyde, nitrosamines, and the like.

To avoid these risks, what are called smoke-free cigarettes are known. These are products in which tobacco is only heated without being burned, so that the desired nicotine is released, albeit in small doses, but the formation of substances harmful to health is prevented. A further approach for a smoke-free cigarette is described in DE 103 21 379 A1. In this smoke-free cigarette, air is heated using an electrical heating device, and the heated air is passed through a nicotine depot. In this regard, the nicotine is supposed to be released by the heated air, to a slight extent, and inhaled by the user. In a further embodiment, the nicotine is directly evaporated from a refillable depot, by means of an electrically operated heating coil, and inhaled by the user through a filter that forms the mouthpiece (see NicStick® cigarette).

These "e-cigarettes," as they are called, do meet the demands made on them with regard to reliability, taste, etc. However, they demonstrate the disadvantage that their heating source must be heated shortly before starting to smoke, specifically by means of providing electrical energy by way of heating spirals or evaporators. Alternatively, charging by means of a rechargeable battery must take place. Therefore provision of energy is required for operation of the smoke-free cigarette. Also, the cigarettes cannot be disposed of in problem-free manner. This is caused by the use of the electrical heating device, which must be disposed of with residual waste. Because this requirement does not exist in the case of traditional cigarettes, because their components, i.e. paper or tobacco leaf, on the one hand, and wrapped tobacco, on the other hand, are materials that biodegrade, a change in thinking must occur at the same time when a user switches from traditional cigarettes to e-cigarettes, but sometimes this does not happen.

SUMMARY OF THE INVENTION

This is where the invention wishes to provide a remedy. The invention is based on the task of creating a heating apparatus for a smoke-free cigarette, which allows reliable release of the nicotine and, at the same time, makes a heating device composed of biodegradable or recyclable material available, which is able to function without provision of external energy. According to the invention, this task is accomplished by a heating apparatus for a smoke-free cigarette that essentially consists of a liquid container and/or a reaction element, which are filled with substances, the mixing of which triggers an exothermic reaction, and which are separated from one another by means of at least one destructible seal.

With the invention, a heating apparatus for a smoke-free cigarette is created, which allows reliable release of the nicotine and, at the same time, makes a heating device composed of biodegradable or recyclable material available, because only two substances, which are not harmful to health and are biologically safe react with one another. By means of mixing the two substances, an exothermic reaction occurs as the result of a chemical reaction between the substances, during which reaction energy is released in the form of heat. In this regard, a temperature can be reached that corresponds to the temperature of the inhaled mixture when smoking traditional cigarettes. The time period of the reaction can be adjusted by way of the size of the liquid container and the amount of the substances. Therefore the properties and the sensation of a traditional cigarette can be replicated with the heating apparatus according to the invention without including their health disadvantages.

In an embodiment of the invention, the liquid container is filled with water. The significant advantage when using water for the exothermic reaction consists in that on the one hand, it can be processed in simple manner and without risks, and on the other hand is non-problematical with regard to environmental criteria.

It is advantageous if the reaction element is filled with calcium chloride. The use of calcium chloride guarantees a reliable exothermic reaction when it encounters the water. As a result, reliable functioning of the heating apparatus according to the invention is guaranteed.

BRIEF DESCRIPTION OF THE DRAWING(S)

Figure 2:
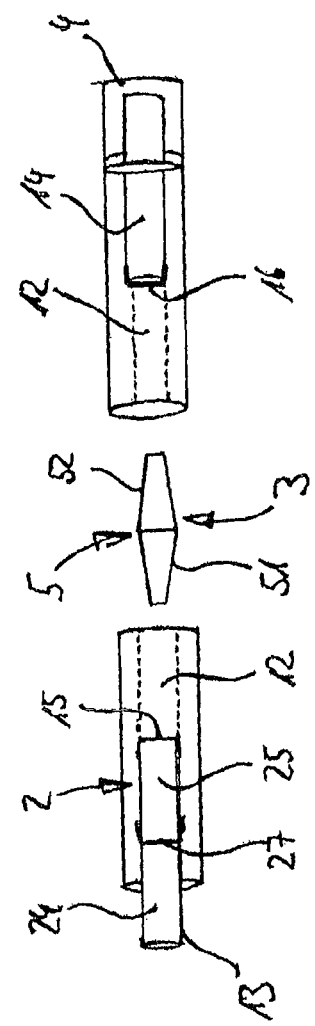
Figure 3:
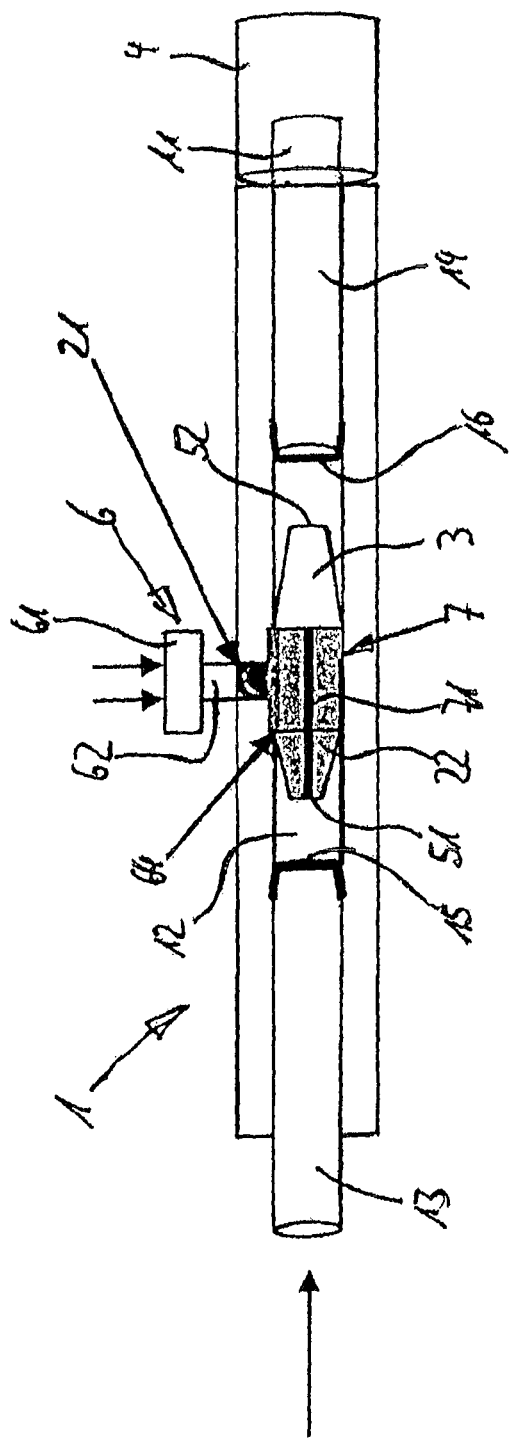
Figure 4:
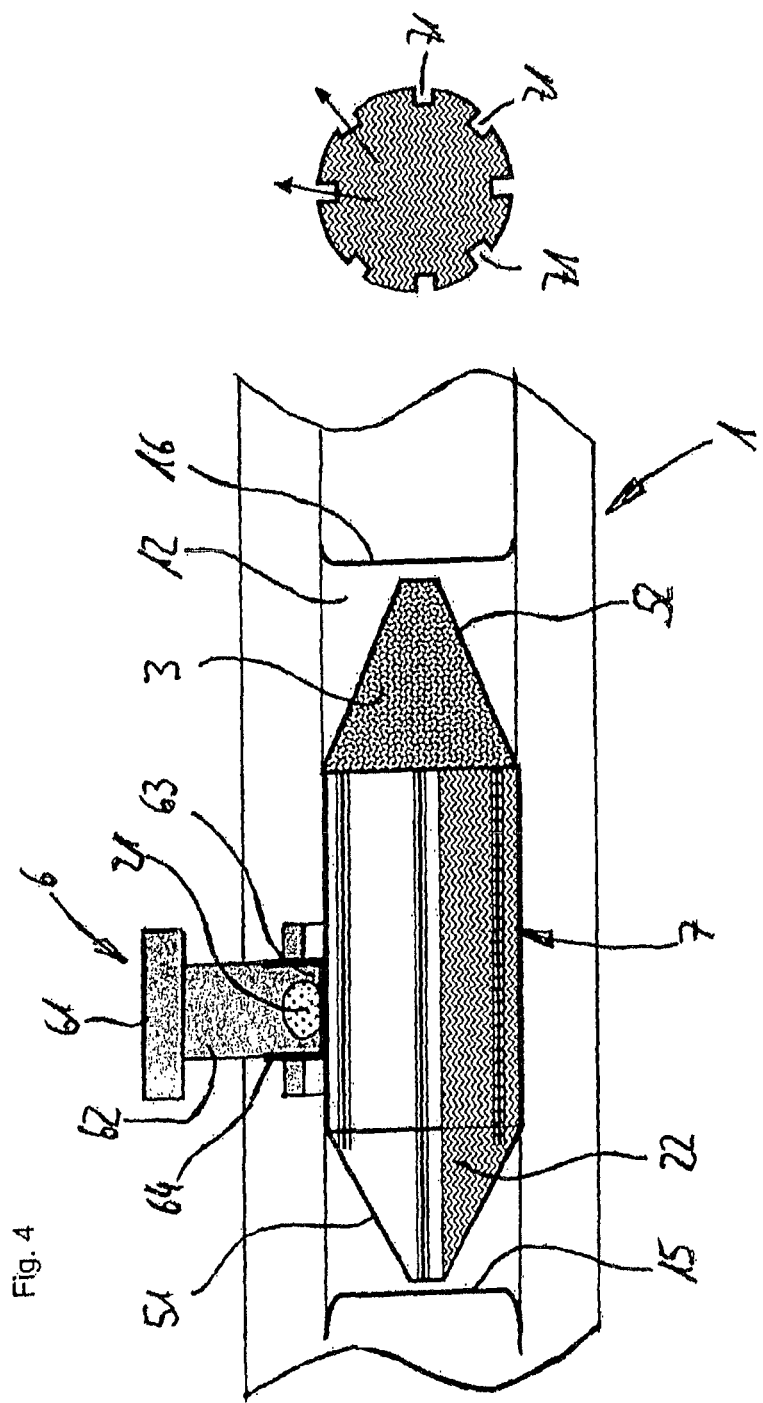
Figure 5:
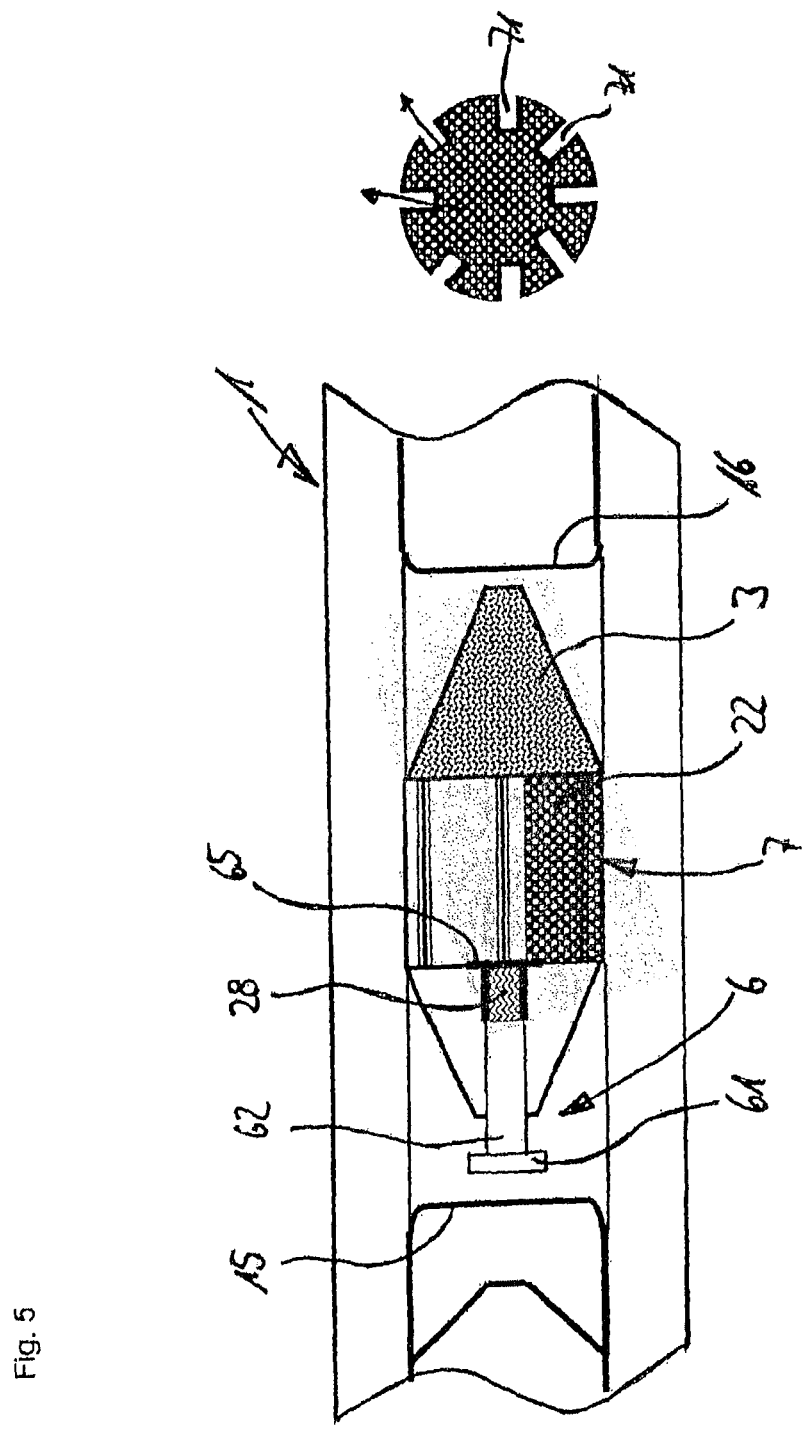
Figure 6:
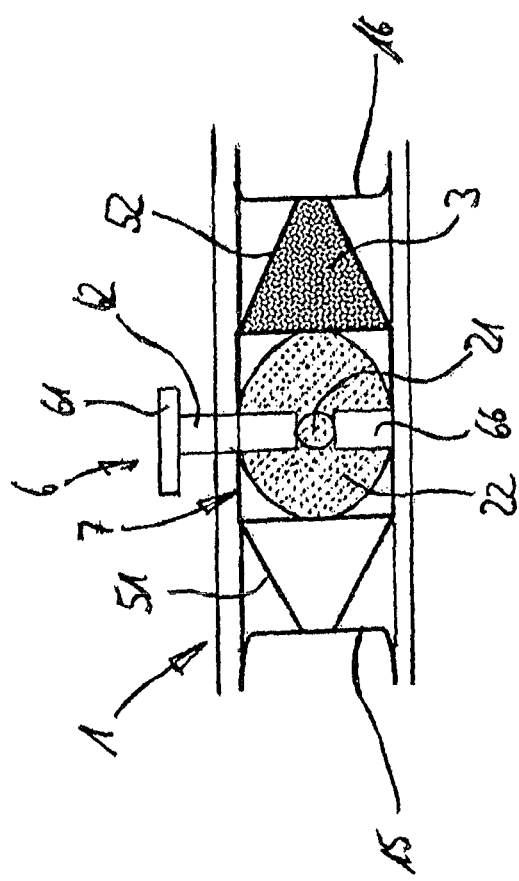
Figure 11:
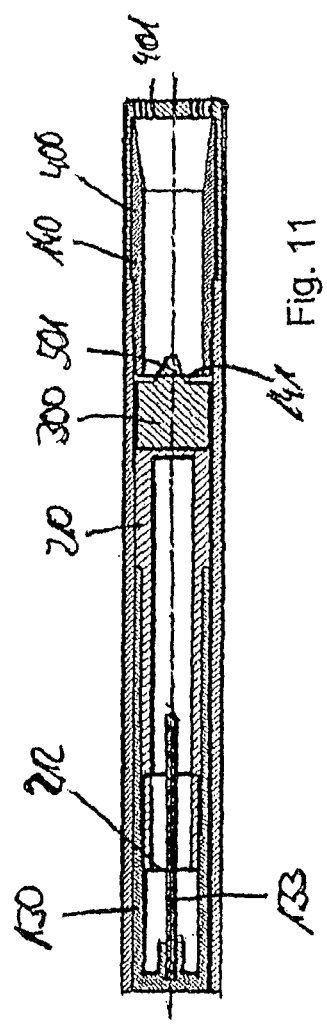
Figure 10:
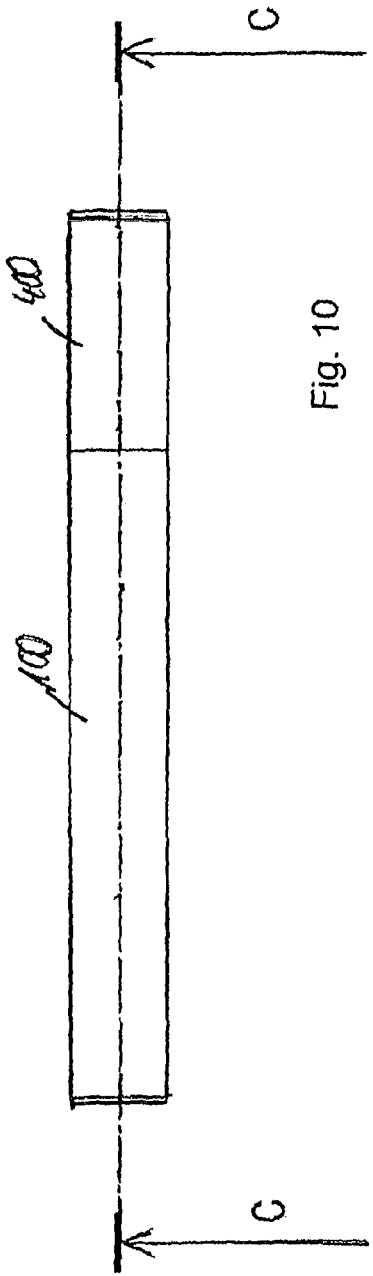
Figure 12:
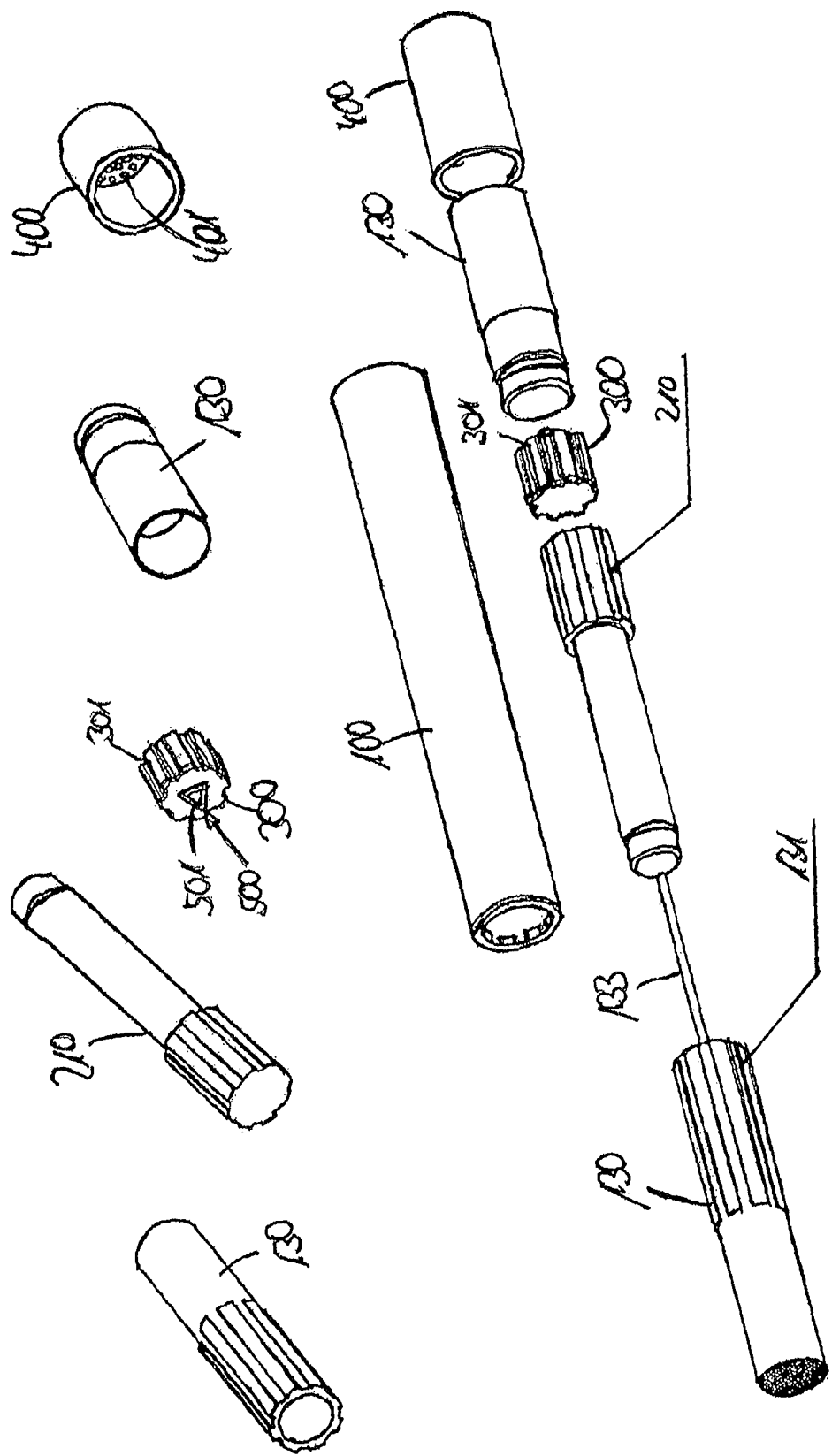
Figure 18:
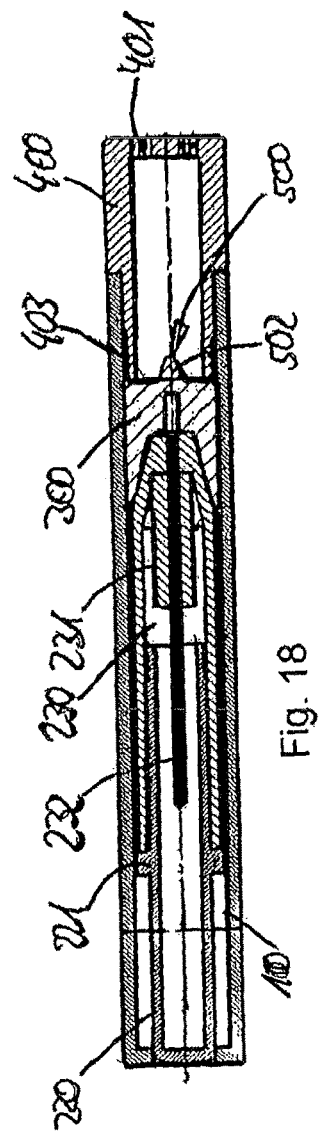
Figure 17:
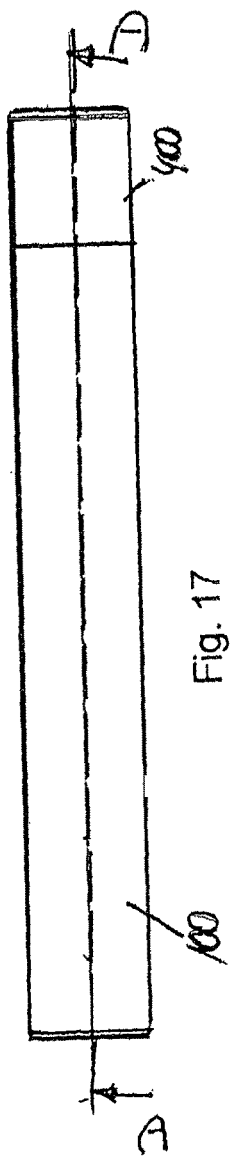
Figure 19:
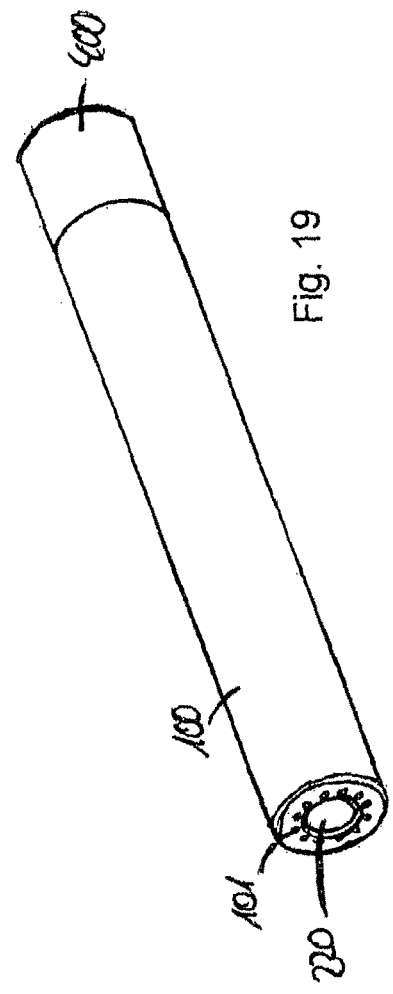
Figure 20:
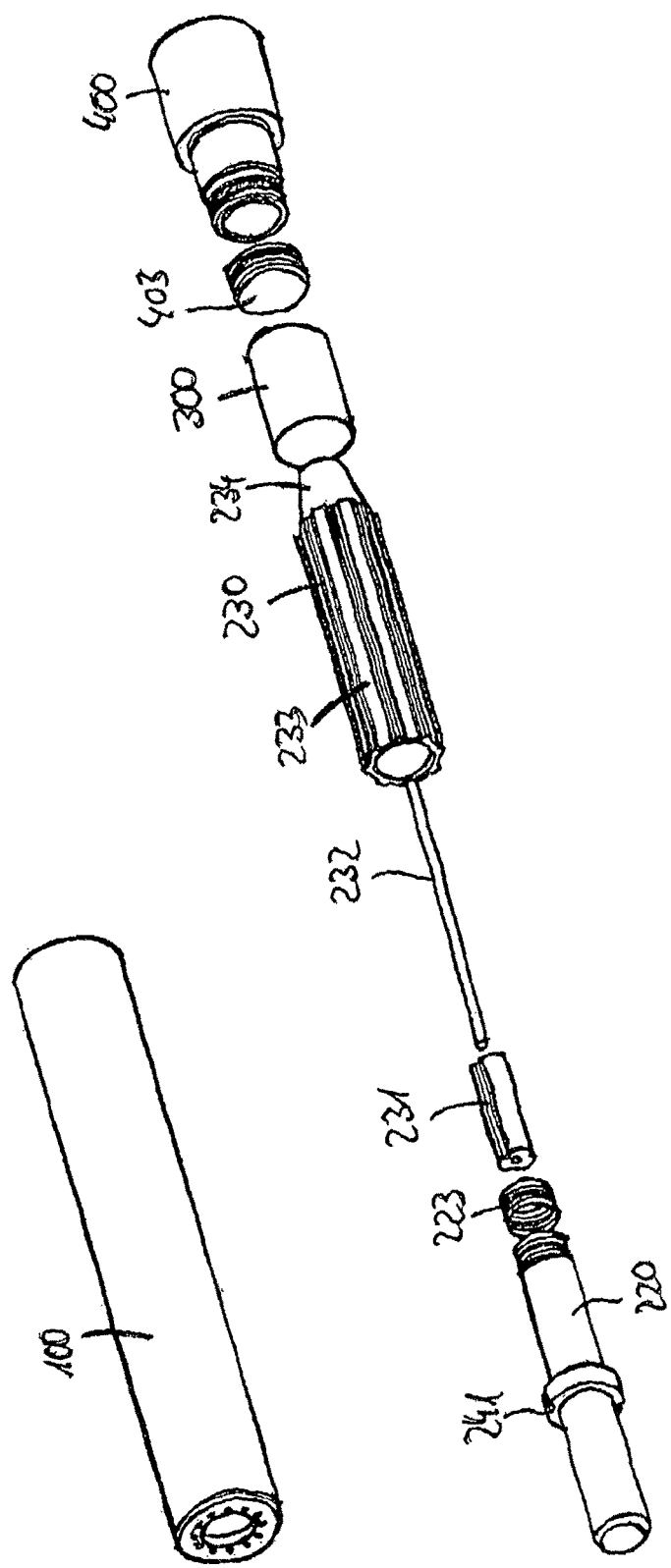

Other further developments and embodiments of the invention are indicated in the remaining dependent claims. Exemplary embodiments of the invention are shown in the drawings and will be described in detail below. The figures show:

FIG. 1 the schematic representation of a smoke-free cigarette having a first heating apparatus according to the invention;

FIG. 2 the schematic representation of a smoke-free cigarette having a second heating apparatus according to the invention;

FIG. 3 the schematic representation of a smoke-free cigarette having a third heating apparatus according to the invention;

FIG. 4 the enlarged representation of the heating apparatus;

FIG. 5 schematic representation of a heating apparatus according to the invention;

FIG. 6 schematic representation of a further heating apparatus according to the invention;

FIG. 7 the view of a smoke-free cigarette having a further heating apparatus according to the invention, in the non-activated state;

FIG. 8 the section along the line A-A in FIG. 7;

FIG. 9 the section along the line B-B in FIG. 7, in an enlarged scale;

FIG. 10 the view of a smoke-free cigarette shown in FIG. 7, in the activated state;

FIG. 11 the section along the line C-C in FIG. 10;

FIG. 12 the exploded representation of the smoke-free cigarette according to FIGS. 7 and 10, as well as its components;

FIG. 13 the view of a smoke-free cigarette with another heating apparatus according to the invention, in the non-activated state;

FIG. 14 the section along the line A-A in FIG. 13;

FIG. 15 the view from the right of the smoke-free cigarette shown in FIG. 13;

FIG. 16 the perspective representation of the smoke-free cigarette shown in FIG. 13;

FIG. 17 the view of the smoke-free cigarette shown in FIG. 13, in the activated state;

FIG. 18 the section along the line D-D in FIG. 17;

FIG. 19 the perspective representation of the smoke-free cigarette shown in FIG. 17;

FIG. 20 the exploded representation of the smoke-free cigarette according to FIGS. 16 and 19, as well as its components;

FIG. 21 the view from the left of the smoke-free cigarette shown in FIG. 13.

DETAILED DESCRIPTION OF THE PREFERRED EMBODIMENTS

In the exemplary embodiments, a smoke-free cigarette is shown, in each instance, which comprises a tubular body 1, 100. A heating apparatus 2, 200 having a reaction partner, and a depot 3, 300 are disposed in the body 1, 100. The smoke-free cigarette has a mouthpiece 4, 400 that follows the depot 3, 300 in the inhalation direction, as well as an activation device 5, 500 for activation of the reaction and/or for release of the inhalation substances. In the exemplary embodiments according to FIGS. 3, 4, and 6, an activation device 6 for triggering the heating apparatus 3 is provided. The smoke-free cigarette is refillable.

The body 1, 100 is produced from paperboard in the exemplary embodiment. In a modification of the exemplary embodiment, other materials, such as biodegradable plastic or metal, for example aluminum, can also be used. The body 1, 100 is configured to be open at its two ends. A cylindrical step 11 is provided at its one end, which serves for setting the mouthpiece 4, 400 on. In the center region of the body 1, 100, an accommodation 12, 120 is furthermore formed, into which the depot 3, 300 can be inserted.

In the exemplary embodiments according to FIGS. 1 to 6, two tubes 13 and 14 can be introduced into the body 1. The tubes 13 and 14 have a membrane 15 and 16, in each instance, on their sides that face one another, which membranes close the tubes 13 and 14 off on one side, in gastight manner. The tubes 13 and 14, just like the body 1, are produced from paperboard or plastic.

The heating apparatus 2 according to FIG. 3 consists essentially of two parts, namely a liquid container 21 and a reaction element 22, which is combined with the depot 3 in a common container 7. Alternatively to the exemplary embodiment, the reaction element 22 can also be disposed in the body 1 separately. On its circumference, the container 7 is provided with grooves 71 that extend on the container 7 in the axial direction, and which allow passage of inhaled air along the depot 3 in the body 1.

The heating apparatus according to FIG. 1 essentially consists of a reaction element 23 that is filled with iron dust. The reaction element 23 is provided with a destructible seal 26 on its side that faces the tube 13.

In the exemplary embodiment according to FIG. 2, a liquid container 24 is provided, which is inserted into the tube 13. In the exemplary embodiment, the liquid container 24 forms the end of the smoke-free cigarette that faces away from the mouthpiece 4. A reaction element 25 is disposed in the tube 13, adjacent to the liquid container 24. The liquid container 24 and the reaction element 25 have different diameters. Due to this configuration, it is possible to push them into one another, at least in certain regions. On their sides that face one another, the liquid container 24 and the reaction element 25 are provided with a destructible seal 27, in each instance.

The reaction elements 23, 25 and the liquid container 24 are provided with grooves on their circumference, which grooves extend in the axial direction and allow passage of inhaled air in the direction of the depot 3.

The liquid containers 21 and 24 are filled with water. The reaction elements 22 and 23 are configured in the manner of a capsule. The reaction element 23 is filled with iron dust; the reaction element 25 with calcium chloride (CaCl) in the exemplary embodiment. Other substances can also be used, for example calcium chloride in the form of $CaCl_2$.

The container having a reaction element 22 is provided or filled with a reaction partner in solid form in the embodiment according to FIG. 3, and after activation and destruction of the sealing membranes 15 and 16 reacts with the ambient air that is drawn in.

The depot 3 is a relatively shape-stable body, composed of sintered material in the exemplary embodiment. Alternatively, nonwoven fabrics or fibrous materials can also be used. The material is gas-permeable and air-permeable. The depot 3 can have different three-dimensional shapes, for example the shape of a cylinder or the like. It is filled with the gaseous medium that is required for the respective application case. If the apparatus is used as a smoke-free cigarette, the depot 3 is filled with nicotine and a carrier substance. Examples of suitable carrier substances are alcohols, esters, ethers, aldehydes, hydrocarbons and mixtures thereof, or also methanol, ethanol, propanol, acetic acid ethyl ester, diethyl ester, acetaldehyde, acetone, pentane, hexane, octane and mixtures thereof can be used as a carrier substance. Also, essential oils can be used as a carrier substance.

In the exemplary embodiments according to FIGS. 1 and 2, the depot 3 simultaneously forms the activation device 5. Here, the depot 3 is provided in a type of double conical stump, in each instance. While the conical stump that faces the tube 13 in the exemplary embodiment according to FIG. 1 forms the reaction element 23, and the conical stump that faces the tube 14 forms the depot 3, the entire double conical stump forms the depot 3 in the exemplary embodiment according to FIG. 2.

In the exemplary embodiment according to FIGS. 3 to 6, a container 7 is provided, which is provided with a cylindrical center part, on the two face-side ends of which the activation device 5 is provided, in each instance, in the form of cutting blades 51 and 52. The cutting blades 51 and 52 are formed by conical tips that extend on both sides of the cylindrical center part of the container 7, in the direction of the tubes 13 and 14. The container is disposed approximately in the region of the center of the body 1 in the assembled state.

The activation device 6 consists of a button 61, which projects radially on the tubular body 1 in the exemplary embodiment according to FIGS. 3, 4, and 6. The button 61 forms the free end of a punch 62 that extends through the covering of the body 1 and on the end of which, facing away from the button 61, an accommodation 63 is provided. In the exemplary embodiment according to FIGS. 3 and 4, the accommodation 63 is surrounded by a destructible seal 64 in certain regions, which seal makes reliable sealing with regard to the reaction element 22 and the liquid container 21 available. The liquid container 21 is disposed in the accommodation 63.

In the exemplary embodiment according to FIG. 5, the button 61 is disposed in the tubular body 1. In this embodiment, as well, it forms the free end of the punch 62, which extends axially along the body 1, however, and an accommodation 63 is likewise provided on the end of the punch that faces away from the button 61. The accommodation 63 accommodates a liquid container 28 that is formed by a reservoir filled with water. The accommodation 63 is separated from the reaction element 22 by means of a destructible seal 65.

In the exemplary embodiment according to FIG. 6, the liquid container 21 is also provided at the free end of the punch 62. It is disposed between punch 62 and a counter-holder 66, and surrounded by the reaction element 22.

Use of the apparatus according to the invention takes place in simple manner. First, placement of the heating apparatus 2 and of the depot 3 in the region of the accommodation 12 of the body 1 takes place. Subsequently, the tubes 13 and 14 can be introduced on both sides of the body 1. After the mouthpiece 4 is set on, the tube 13 projects out of the body 1. By pressing the tube 13 in, the cutting blade 51 that faces the tube passes through the membrane 15, so that the gastight closure is opened on one side. By further introducing the tube 13 into the body 1, the second cutting blade 52 on the side facing the tube 14 also passes through the membrane 16 provided there, so that now, it is possible to draw in air and the gas situated in the depot 3.

In the exemplary embodiment according to FIG. 1, triggering of the heating apparatus 2 takes place by means of the reaction of the iron dust situated in the reaction element 23 with the ambient air that comes into contact with the iron dust after the membrane 15 is pierced. This contact releases an exothermic reaction, because the iron contained in the iron dust begins to rust autocatalytically upon contact with the air. In this way, heat is released and a temperature of approximately 85 to 100° C. is reached. When ambient air is drawn in by the user, into the tube 13, this air moves past the reaction element 23 through the grooves, and during this process is heated to approximately 50° C. on the basis of the heat released by the reaction, thereby achieving an inhalation temperature that is comparable to that of traditional cigarettes. The nicotine is dissolved out of the depot with the warm air, after this air moves past the reaction element 23, and inhaled by the user after the air moves past the mouthpiece.

In the exemplary embodiment according to FIG. 2, triggering of the heating apparatus 2 takes place by means of the reaction of the water in the liquid container 24 with the calcium chloride in the reaction element 25. This is brought about by means of penetration of the liquid container 24 into the reaction element 25, at least in certain regions, or vice versa. In this way, too, an exothermic reaction is triggered, in other words a chemical reaction takes place between the calcium chloride and the water, during which reaction energy is released in the form of heat, which can reach a temperature of up to 100° C. When the user draws in air, the process described above with regard to the exemplary embodiment according to FIG. 1 takes place, so that the nicotine can be inhaled with warm air.

In the exemplary embodiment according to FIGS. 3 to 6, the activation device 6 is used for triggering the heating apparatus 2. By pressing the button 61 on the tubular body 1 radially inward, as this button is shown in FIGS. 3, 4, and 6, the liquid container 21, which is filled with water, is pressed through the membrane 15 into the reaction element 22; in the exemplary embodiment according to FIG. 5, this takes place as they are pushed together in the axial direction. The exothermic reaction described above is triggered by means of the contact of the calcium chloride with the water.

In the exemplary embodiment according to FIGS. 7 to 12, a tube 140 is set into the mouthpiece 400 that is provided with exit openings 401. The tube 140 has a membrane 141 on its side facing the depot 300, which membrane closes the tube 140 off in gastight manner on one side. The membrane 141 preferably consists of aluminum. On the side facing away from the mouthpiece 400, a displaceable liquid container 130 is disposed in the cigarette body 100. The liquid container 130 is provided with axially oriented grooves 131 on its circumference. On the inside, the liquid container 130 is provided with a step 132. A pin 133 is provided in the liquid container 130, coaxial to its longitudinal center line, which pin extends over about half the length of the liquid container 130. The pin 133 consists of heat-conductive, preferably biodegradable plastic or metal, for example aluminum. The tube 140 and the liquid container 130, just like the body 100, are produced from paperboard, metal, for example aluminum, or plastic. The liquid container 130, which is filled with water, can be coated with wax on the inside in the case of the embodiment in the form of paperboard.

As can particularly be seen in FIGS. 8 and 11, a reaction element 210 is provided in the cigarette body 100, which element lies against the inside of the cigarette body 100 with its outer surface on its side facing the depot 300. On the outside, it is provided with a step 211 that brings about a reduction in the outside diameter on the side facing away from the depot 300. In this region, the reaction element 210 has an outside diameter that essentially corresponds to the inside diameter of the liquid container 130 on the side facing the depot 300, so that the reaction element 210 can move into the liquid container 130 in certain regions. On its side facing away from the depot 300, the reaction element 210 has a seal 212 that closes the reaction element 210 off in gastight manner on one side. The seal 212 consists of plastic film or aluminum foil. In the region adjacent to the step 211, the reaction element 210 is provided with grooves—not shown—on the outside. The reaction element 210 stands in direct contact with the depot 300 with its face-side end. The reaction element 210 consists of heat-conductive plastic or metal, with corrosion-resistant iron or aluminum preferably being used. It is filled with calcium chloride as loose bulk material and with a hydrophobic fat derivative.

The fat derivative can have different compositions; preferably, a stearyl alcohol derived from stearic acid is used. Fundamentally, fats and fatty oils (neutral fats) are esters of the trivalent alcohol glycerin (propane-1,2,3-triol) with three, generally different, predominantly even-numbered and non-branched aliphatic monocarboxylic acids, called fatty acids. Compounds of this type are also called triglycerides or triacylglycerols. Fats present in natural form are classified as lipids, for example triacylglycerides, phospholipids, sphingolipids or lipids produced from isopentenyl pyrophosphate.

Lipids is a collective term for natural substances that are entirely or at least for the most part insoluble in water (hydrophobic). Several groups of differently structured molecules are covered by the term lipids, namely lipids with and without ester bonds, fatty acids and their derivatives, as well as isoprene derivatives. They can be classified as follows, in accordance with the alcohol involved, in each instance: waxes (long-chain alcohol), glycerolipids (containing glycerin), sphingolipids (containing sphingosine), and cholesterol esters (hydroxyl group of cholesterol serves as the alcoholic group).

The depot 300 can have different three-dimensional shapes; in the exemplary embodiment according to FIGS. 7 to 12, it essentially has the shape of a cylinder, which is provided with grooves 301 on the outside (see FIG. 12). On the side facing the mouthpiece 400, the depot 300 is provided with the activation device 500 in the form of a mandrel 501.

In the exemplary embodiment according to FIGS. 13 to 21, the mouthpiece 400 is inserted into the cigarette body 100. For this purpose, it is provided with a stop 402 on the outside. The mouthpiece 400, which is provided with exit openings 401, is tightly sealed by means of a membrane 403. The membrane 403 preferably consists of aluminum foil.

On the side facing away from the mouthpiece 400, the cigarette body 100 is provided with entry openings 101. A displaceable liquid container 220 is disposed in the cigarette body 100, which container is filled with water and consists of heat-conductive plastic or metal, with corrosion-resistant iron or aluminum preferably being used. The liquid container 220 has a stop 221 on its circumference, which closes off the entry openings 101 in the non-activated state. The liquid container 220 has a seal 223 on its side facing the depot 300, which closes the liquid container 220 off on one side, in gastight manner. In the exemplary embodiment, the seal 223 consists of aluminum. Other materials are also possible.

A reaction element 230 is displaceably disposed in the cigarette body 100. The reaction element 230 is configured in the manner of a tube closed on one side. In the exemplary embodiment, it is produced as a molded body, for example filled with dried calcium chloride or an earth alkali metal. The reaction element 230 has a slightly smaller outside diameter than the inside diameter of the cigarette body 100. The reaction element 230 is provided with axially oriented grooves 233 on its circumference. On the side facing the depot 300, the reaction element 230 has a tip 234 in the shape of a conical stump. On the inside, a profile body 231 is provided at the end facing the depot 300. In the exemplary embodiment, the profile body 231 is produced from earth alkali metal, for example lithium, sodium, potassium or calcium. However, it can also be produced from calcium chloride (CaCl), calcium chloride ($CaCl_2$), magnesium sulfate ($MgSO_4$), sodium hydroxide (NaOH) or calcium oxide (CaO). The profile body 231 has grooves on its mantle surface, in the longitudinal direction. It has an outside diameter that is smaller than the inside diameter of the reaction element 230.

The profile body 231 is set onto the pin 232, which extends coaxially to the longitudinal center line of the reaction element 230. The pin 232 passes through the profile body 231 completely and, in the exemplary embodiment, extends through the tip, in the shape of a conical stump, of the reaction element 230, all the way into the depot 300. It can be inserted into the tip of the reaction element 230 or can directly be a component of the reaction element 230. The pin 232 consists of biodegradable, heat-conductive plastic or metal.

The depot 300 has the activation device 500 in the form of a mandrel 502 on its side facing the mouthpiece 400. It has a recess in the shape of a conical stump on the side facing away from the mouthpiece 400, which recess accommodates the tip 234, in the shape of a conical stump, of the reaction element 230.

In the exemplary embodiments according to FIGS. 7 to 21, the depot 300 has a relatively shape-stable body, composed of sintered material in the exemplary embodiments. Alternatively, nonwoven fabrics or fibrous material can also be used. The material is gas-permeable and air-permeable. The depot 300 is filled with the gaseous medium required for the respective application case. If the apparatus is used as a smoke-free cigarette, the depot 300 is filled with nicotine and a carrier substance. Examples of suitable carrier substances are alcohols, esters, ethers, aldehydes, hydrocarbons and mixtures thereof; or also methanol, ethanol, propanol, acetic acid ethyl ester, diethyl ether, acetaldehyde, acetone, pentane, hexane, octane and mixtures thereof can be used as a carrier substance. Also, essential oils can be used as a carrier substance.

In the exemplary embodiments according to FIGS. 7 to 21, activation of the heating apparatus for a smoke-free cigarette takes place by means of compression of the displaceable parts. In the exemplary embodiment according to FIGS. 7 to 12, the liquid container 130 is pressed into the cigarette body 100. As a result, the pin 133 comes into contact with the seal 212. By pushing the liquid container 130 in further, the pin 133 penetrates the seal 212. In this manner, water from the liquid container 130 comes into contact with the bulk calcium chloride with fat derivative in the reaction element 210, thereby causing an exothermic reaction. The fat derivative used brings about the result, in this regard, that not only the calcium chloride that comes directly into contact with the water reacts, but rather the entire calcium chloride situated in the reaction element 210 participates in the exothermic reaction. The water reacts with the calcium chloride and the hydrophobic fatty phase of the stearyl alcohol is "blasted off" and releases the next calcium chloride phase, which is ready to react, so that the reaction continues over the entire reaction space. The interaction of the liquid container 130 and the reaction element 210 as well as the exothermic reaction triggered by their contents forms the heating apparatus 200. The liquid container 130 is pressed into the cigarette body 100 until the face-side end of the liquid container 130 makes contact with the step 211 of the reaction element 210. If further pressure is exerted on the liquid container 130, the reaction element 210 is then also displaced axially in the cigarette body 100. This brings about displacement of the depot 300, as well. In this process, the activation device 500 in the form of the mandrel 501 passes through the membrane 141 (see FIG. 11). As a result, it is possible for the user to draw air in. This air enters into the cigarette body 100 through the grooves 131 on the end facing away from the mouthpiece 400, and along the liquid container 130 and the reaction element 210, along the depot 300, into the tube 140 and from there through the exit openings 401 in the mouthpiece 400. As it moves past the reaction element 210, the air is heated to approximately 50° C. due to the heat released by the reaction, and thereby an inhalation temperature comparable to traditional cigarettes. The nicotine is dissolved out of the depot 300 by the warm air after it moves past the reaction element 210. The warm air then enters into the tube 140 through the opening in the membrane 141 caused by the mandrel 501, and is inhaled by the user after it passes through the mouthpiece 400.

In the exemplary embodiment according to FIGS. 13 to 21, the liquid container 220 is pressed into the cigarette body 100. As a result, the seal 223 comes into contact with the pin 232. By pushing the liquid container 220 in further, the pin 232 penetrates the seal 223. In this manner, water in the liquid container 220 comes into contact with the profile body 231, thereby bringing about an exothermic reaction. The interaction of the profile body 231 and of the liquid container 220 as well as the exothermic reaction triggered thereby forms the heating apparatus 200. The liquid container 220 is pressed into the cigarette body 100 until the stop 221 makes contact with the face-side end of the reaction element 230. When further pressure is exerted on the liquid container 220, the reaction element 230 is then also displaced axially in the cigarette body 100. This simultaneously brings about displacement of the depot 300. During this process, the activation device 500 in the form of the mandrel 502 passes through the membrane 403 in the mouthpiece 400 (see FIG. 18). This makes it possible for the user to draw air in. This air enters into the cigarette body 100 through the entry openings 101 at the end facing away from the mouthpiece 400 and moves along the liquid container 220 and the reaction element 230 along the depot 300 into the mouthpiece 400 and through the exit openings 401. As it moves past the reaction element 230, the air is heated to approximately 50° C. by the heat released due to the reaction, thereby achieving an inhalation temperature that is comparable to traditional cigarettes. The nicotine is dissolved out of the depot 300 by the warm air after it moves past the reaction element 230. Afterward, the warm air enters into the mouthpiece 400 through the opening in the membrane 403 caused by the mandrel 502 and is inhaled by the user after it moves past the mouthpiece 400. Due to the projection of the pin 232 all the way into the depot 300, heating of the depot 300 from the inside is also achieved, leading to improved mobilization of the nicotine from the depot 300 and thereby to an improved degree of effectiveness.

In a modification of the exemplary embodiments shown in FIGS. 7 to 21, the possibility also exists of producing the seals and/or the membranes from materials other than aluminum. Plastic films or varnishes are particular possibilities here. What is essential for the material selected is the property of sealing the respective component tightly so that it is non-sensitive to climatic variations and has sufficient brittleness to guarantee reliable penetration by the pins and mandrels. The seals and membranes protect the system as a whole from drying out and from evaporation of the ingredients before it is put into operation.

Furthermore, in a modification of the exemplary embodiments shown, the possibility also exists of using the functional structure of the exemplary embodiment according to FIGS. 13 to 21 in the heating apparatus according to FIGS. 7 to 12 and vice versa. Thus, a profile body comparable to the profile body 231 according to FIGS. 13 to 21 can be set onto the pin 133. In this case, the reaction element 210 is filled with water. Likewise, the possibility exists of using the functional structure of the exemplary embodiment according to FIGS. 7 to 12 in the heating apparatus according to FIGS. 13 to 21. In this case, the profile body 231 set onto the pin 232 is eliminated. Furthermore, in this case the container 220 is filled with a loose bulk material, for example composed of calcium chloride and a hydrophobic fat derivative, and the reaction element 230 is filled with water. In this case, the exothermic reaction takes place as described above.

The exothermic reaction takes place over a period of three to five minutes, based on the size of the liquid containers or of the reaction elements, respectively, and their content; this corresponds to the period of time for smoking traditional cigarettes. Consequently, a smoke-free cigarette is created by the heating apparatus according to the invention, which simulates the properties and the sensation of a traditional cigarette without containing its health disadvantages. Furthermore, because of the very efficient reaction, the depot only has to be filled with 10 mg of nicotine in order to achieve an effect comparable to traditional cigarettes over the entire period of time. In the case of the solutions known from the state of the art, approximately 18 mg are required. If swallowed, this can be a dosage that is extremely hazardous to health, if not fatal.

The invention claimed is:

1. A smoke-free cigarette comprising:
    a tubular cigarette body;
    a mouthpiece inserted in the cigarette body, the mouthpiece having a membrane;
    a depot situated in the cigarette body, the depot being filled with nicotine and a carrier substance;
    a heating apparatus; and
    an activation device for triggering the heating apparatus, the activation device comprising a mandrel;
    wherein the heating apparatus comprises
        a liquid container filled with a substance, and
        a reaction element produced from a substance;
    wherein mixing of these substances triggers an exothermic reaction, and the substances are separated from one another by means of at least one destructible seal;
    wherein a pin composed of heat-conductive plastic or metal is provided on the reaction element, the pin interacting with the seal, and onto the pin a profile body being set;
    wherein the profile body is produced from an earth alkali metal, calcium chloride, calcium chloride, magnesium sulfate, sodium hydroxide or calcium oxide;
    wherein the liquid container comprises a stop;
    wherein the reaction element has a longitudinal center line and comprises a face-side end and a tip shaped as a conical stump;
    wherein the pin extends coaxially to the longitudinal center line of the reaction element and passes through the profile body completely and extends through the tip into the depot;
    wherein the liquid container is pushable into the reaction element so that the stop of the liquid container makes contact with the face-side end of the reaction element;
    wherein the pin is configured to penetrate the seal by pushing the liquid container into the reaction element; and
    wherein the reaction element is axially displacable in the cigarette body, and is configured to be axially displaced if pressure is exerted on the liquid container after the stop makes contact with the face-side end of the reaction element to bring about displacement of the depot in such a way that the mandrel passes through the membrane in the mouthpiece.

2. The smoke-free cigarette according to claim 1, wherein the liquid container is filled with water.

3. The smoke-free cigarette according to claim 1, wherein the reaction element is filled with calcium chloride and a fat derivative.

4. A smoke-free cigarette comprising:
a tubular cigarette body;
a depot situated in the cigarette body, the depot being filled with nicotine and a carrier substance;
a heating apparatus; and
an activation device for triggering the heating apparatus, the activation device comprising an accommodation;
wherein the heating apparatus comprises
  a liquid container disposed in the accommodation and filled with a substance and
  a reaction element that is produced from a substance;
wherein mixing of these substances triggers an exothermic reaction, and the substances are separated from one another by means of at least one destructible seal;
wherein a pin composed of heat-conductive plastic or metal is provided on the reaction element, the pin interacting with the seal, and onto the pin a profile body being set; and
wherein the profile body is produced from an earth alkali metal, calcium chloride, calcium chloride, magnesium sulfate, sodium hydroxide or calcium oxide.

* * * * *